United States Patent [19]
Graham et al.

[11] 3,952,582
[45] Apr. 27, 1976

[54] ULTRASONIC INSPECTION DEVICE AND SYSTEM

[75] Inventors: Joe D. Graham, Poway; Kenneth W. Mead; Henry Edgar Babb, both of El Cajon, all of Calif.

[73] Assignee: Carpenter Technology Corporation, Reading, Pa.

[22] Filed: Mar. 7, 1975

[21] Appl. No.: 556,422

[52] U.S. Cl............................ 73/67.8 S; 73/71.5 US
[51] Int. Cl.²......................................... G01N 29/04
[58] Field of Search.................. 73/67.8 S, 71.5 US, 73/67.7

[56] References Cited
UNITED STATES PATENTS

| | | | |
|---|---|---|---|
| 3,068,370 | 12/1962 | McInnish | 73/67.7 X |
| 3,159,756 | 12/1964 | Beaujard et al. | 73/67.8 S X |
| 3,190,112 | 6/1965 | Beaujard et al. | 73/71.5 US |
| 3,413,843 | 12/1968 | Kortenhoven | 73/67.8 S X |
| 3,824,843 | 7/1974 | Gebeshuber et al. | 73/71.5 US |

*Primary Examiner*—Charles A. Ruehl
*Attorney, Agent, or Firm*—Edgar N. Jay

[57] ABSTRACT

An ultrasonic measuring system particularly suited for measuring the wall thickness of large tubing of widely different shapes and sizes. An ultrasonic transducer is adjustably supported in an ultrasonic head assembly so as to provide precise focusing of the energy across a gap to the surface of the part being measured. The head assembly is urged against the surface of the part while the two are displaced relative to one another so that the transducer scans a predetermined path along the part. Freely rotatable balls carried by the head assembly engage the surface of the part while a column of water is maintained to fill the gap between the transducer and the surface of the part. Provision is made for rotating circular parts so that the transducer sweeps out a spiral path over the surface of such parts. In the case of non-circular parts, the head assembly is oscillated from side-to-side while the part and the head are moved relative to one another along the longitudinal axis of the part so that the transducer sweeps out a sinusoidal path over a side of the part.

7 Claims, 3 Drawing Figures

ULTRASONIC INSPECTION DEVICE AND SYSTEM

BACKGROUND OF THE INVENTION

This invention relates to ultrasonic measuring devices and a system incorporating the same for ultrasonically measuring or inspecting metal tubing having a wide variety of shapes and sizes.

Hitherto, objects to be measured or tested ultrasonically have been immersed in a body of water adjacent to one or more transducers. However, particularly in the case of large objects such as long lengths of tubing of substantial diameter, such arrangements have left much to be desired. One drawback has resided in the difficulty of maintaining precise alignment and spacing between the object being measured and the transducer. Another drawback has been the need to suppress or eliminate algae which tend to grow in the water and to prevent the formation of bubbles which result in spurious readings.

It has also been hitherto recognized that the disadvantages of completely immersing large objects in a body of water for coupling with an ultrasonic transducer can be largely minimized by maintaining a column or stream of water between the ultrasonic transducer and the part being inspected. Apparatus has been provided for inspecting and/or measuring parts ultrasonically, utilizing a column of water as the coupling medium instead of immersing all or relatively large portions of the part; but such apparatus has been found to be unsuited for the inspection and measurement of tubing to the exacting standards required to be met in the manufacture of large, precision tubes free from surface blemishes from alloys containing zirconium, columbium, tantalum or hafnium, as well as high temperature alloys and stainless steels.

SUMMARY OF THE INVENTION

It is, therefore, a principal object of this invention to provide an ultrasonic measuring device and a system incorporating the same which facilitates to a unique degree ultrasonic inspection and wall thickness measurement of large parts without immersing the part in water which is particularly well suited for use with large tubing whether circular or non-circular in cross section, and whether or not the part has substantially constant exterior dimensions while at the same time minimizing and, for practical purposes, eliminating the likelihood of even slight damage to the contacted surface of the part.

A more specific object is to provide such an ultrasonic measuring device including transducer mounting means which facilitates accurate alignment of the transducer with the part, which relationship is accurately maintained throughout the scanning of the part.

Another specific object is to provide such an ultrasonic measuring device which maintains the transducer in predetermined relation to the surface of the part being scanned even when the surface incorporates substantial changes in contour, and which also can be readily adapted for use with widely different sizes and shapes all while leaving the surface of the part undergoing test remarkably free of surface marks or blemishes.

In carrying out the present invention, there is preferably provided a resiliently biased support for an ultrasonic head assembly in which a transducer is adjustably supported to permit accurate focusing of the acoustical energy across a gap onto the surface of the part engaged and scanned by the head assembly. The head assembly is urged against the part undergoing inspection while the two are displaced relative to one another so that the transducer scans a predetermined path along the part. As is well known, the transducer functions as a transmitter and receiver so that signals representative of front and back surface echoes or reflections from the part are utilized in a known way to provide a D.C. output voltage proportional to the time lapse between them which is then readily converted to a thickness measurement.

DESCRIPTION OF THE DRAWINGS

The foregoing, as well as additional objects and advantages of the present invention, will be apparent from the following detailed description of the preferred embodiment and the accompanying drawing in which.

DESCRIPTION OF THE PREFERRED EMBODIMENTS

Figure 1:
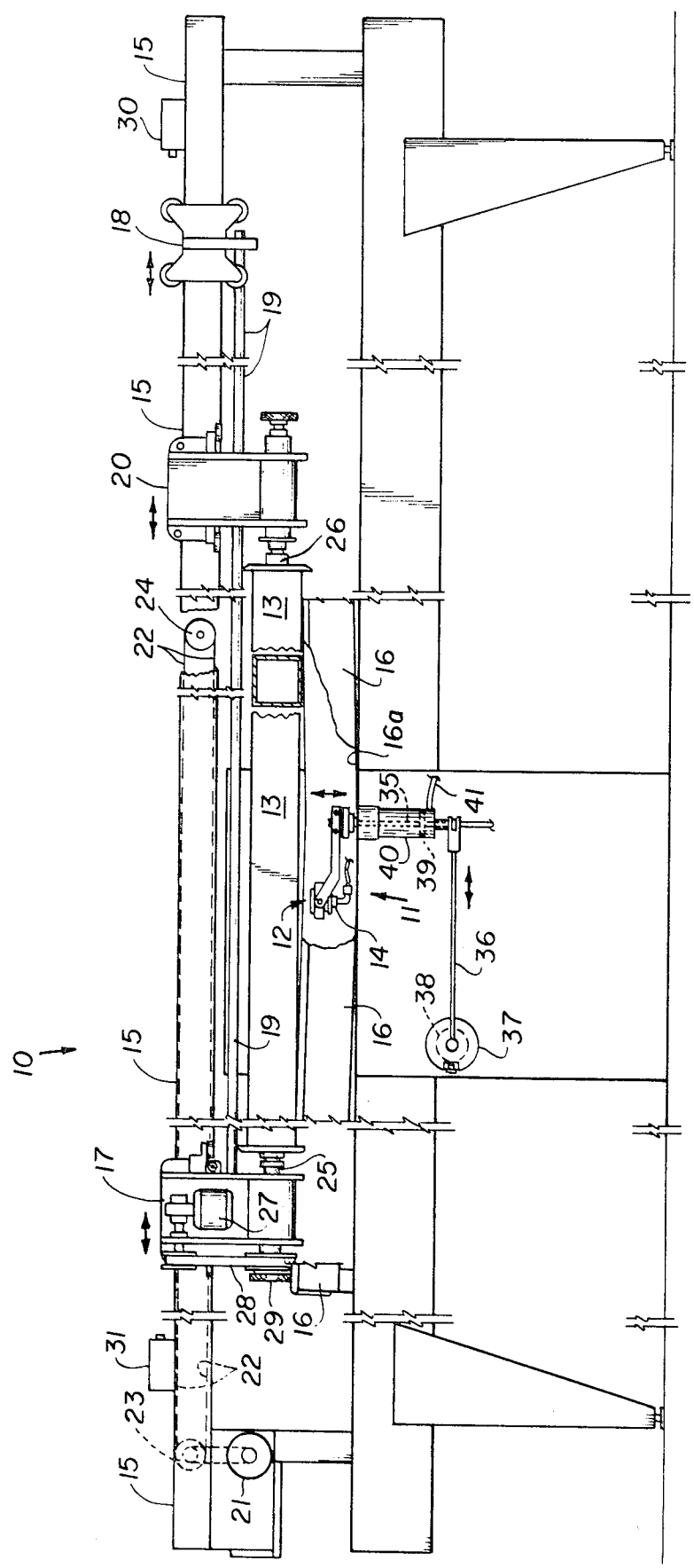
FIG. 1 is an elevational view, partially diagrammatic, of an ultrasonic inspection and measuring system constructed in accordance with the present invention.
Figure 2:
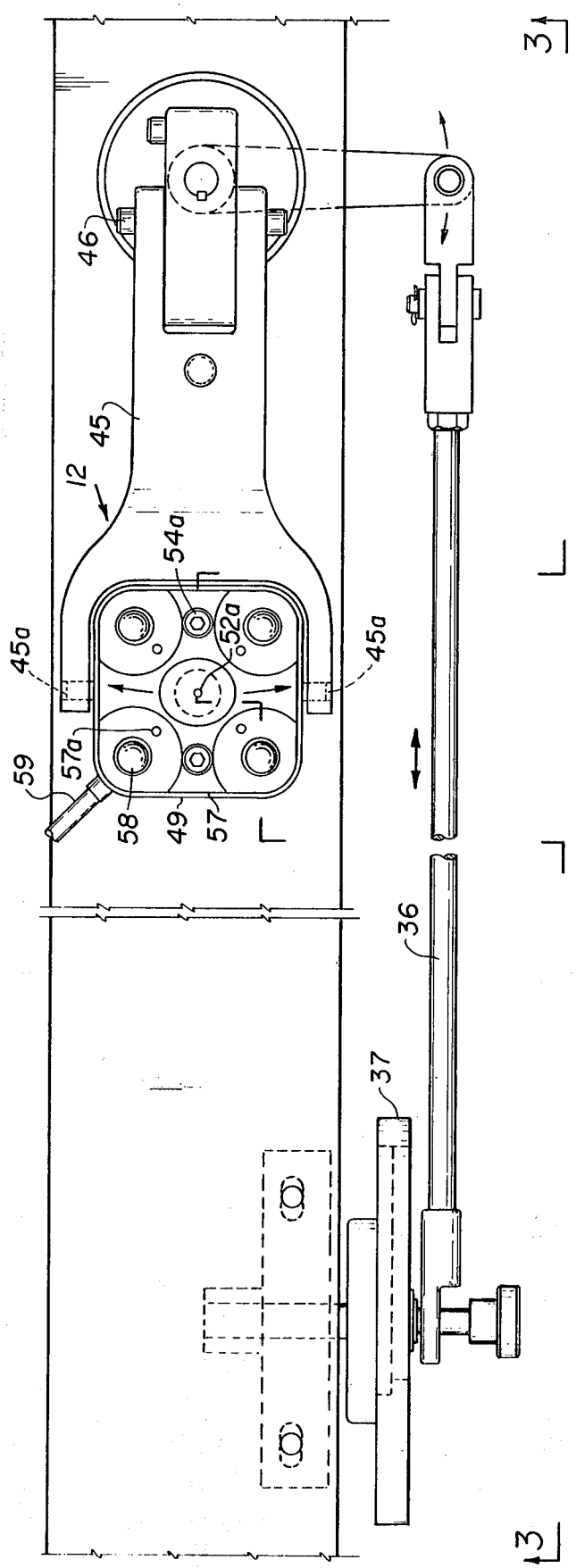
FIG. 2 is a plan view, on an enlarged scale, of the ultrasonic head assembly together with its support and drive means.

Referring now to the drawings in detail, ultrasonic measuring system 10 comprises a measuring station indicated generally at 11 where an ultrasonic head assembly 12 is maintained in predetermined relation to the surface of a part 13. As will be more fully pointed out hereinafter, the head assembly 12 is preferably resiliently biased against the surface of the part 13 while they are mutually displaced relative to one another so that an ultrasonic transducer 14 carried by head assembly 12 sweeps out a predetermined path along the surface of the part. In the case of tubes which are arcuate in cross section, the head assembly 12 preferably is maintained stationary while the tube undergoing inspection is displaced longitudinally and is simultaneously rotated so that the head assembly 12 and the transducer 14 carried thereby sweep out a desired spiral path over the surface of the tube. When the part 13 undergoing inspection is a tube which is polygonal in cross section as shown in FIG. 1, then the tube is displaced longitudinally and is not rotated on its axis, but, instead, the head assembly 12 is oscillated from side-to-side so that transducer 14 sweeps out a more or less sinusoidal path along one side of the tube. And depending upon how many sides the tube may have and the number thereof to be inspected, as many passes would be required.

For supporting and rotating and/or longitudinally displacing tubing undergoing inspection, a rail 15 is supported adjacent to a catch pan 16. Means for supporting and displacing the tubing 13 in relation to the head assembly 12 include a drive carriage assembly 17 and a tie bar carriage assembly 18 which are movably supported on rail 15 and fixed in spaced relation by means of a tie bar 19 by which they are interconnected so that displacement of the drive carriage assembly 17 along rail 15 is imparted to the tie bar carriage assembly 18. To permit the system to be readily adapted to receive parts of widely different lengths, a tail carriage assembly 20 is movably supported on rail 15, and is adapted to be clamped in any desired position along the length of tie bar 19 by means of one or more clamps not shown.

The drive carriage assembly 17 can be moved along the rail 15 in any convenient way. As shown in FIG. 1, motor 21, through a reversible gear train controlled by means of electric clutches (not shown) drives a cable 22, both ends of which are connected to the drive carriage assembly 17, to form an endless loop, the left end of which engages drive pulley 23 and the right end of which (as viewed in FIG. 1) passes around idler 24. Thus, the upper and lower courses of the cable 22 serve to propel the drive carriage assembly 17 together with tie bar carriage assembly 18, tie bar 19 and tail carriage assembly 20 to the right or left along rail 15 as required.

A drive spindle 25 rotatably mounted on the drive carriage assembly 17 and an idler spindle 26 rotatably carried by the tail carriage assembly 20 support the part 13 to be inspected between them. A drive motor 27, when energized, rotates the part 13 through a suitable power train 28 which can be disengaged from the drive spindle 25 by means of a clutch 29 to facilitate manual rotation of spindle 25 when that is desired.

As shown in FIG. 1, the drive carriage assembly 17 is shown near the end of its forward (right) motion with tie bar carriage assembly 18 near right limit switch 30 which is movably supported adjacent to rail 15 or, if desired, can be mounted on the drive carriage assembly 17 for engagement with a suitably located stop.

Catch pan 16 is elongated and is located so as to underlie wherever water may drip from the part undergoing inspection. The ultrasonic head assembly 12 is vertically movably supported in the catch pan 16 by resilient biasing means comprising a shaft 35 of an air cylinder 40 extending through an opening formed in the base 16A of the catch pan 16. As is well known, the shaft 35 of the air cylinder 40 carries a piston 39 by which it is raised by air under pressure supplied through air hose 41 and controlled through a valve not shown. The lower end of shaft 35 is connected by means of rod 36 to a crank 37 driven by motor 38. When motor 38 is energized, it serves to oscillate shaft 35 about its vertical axis for a purpose yet to be described, and when motor 38 is energized, drive motor 27 for rotating part 13 is normally not energized.

It may be well to note here that the several motors, clutches and the air control valve together with various switches including those shown and described herein and others are connected to a suitable source of electrical power in keeping with good electrical practice. Because such arrangements are well known and do not form any part of the present invention, a more detailed description thereof will not be provided here.

Figure 3:
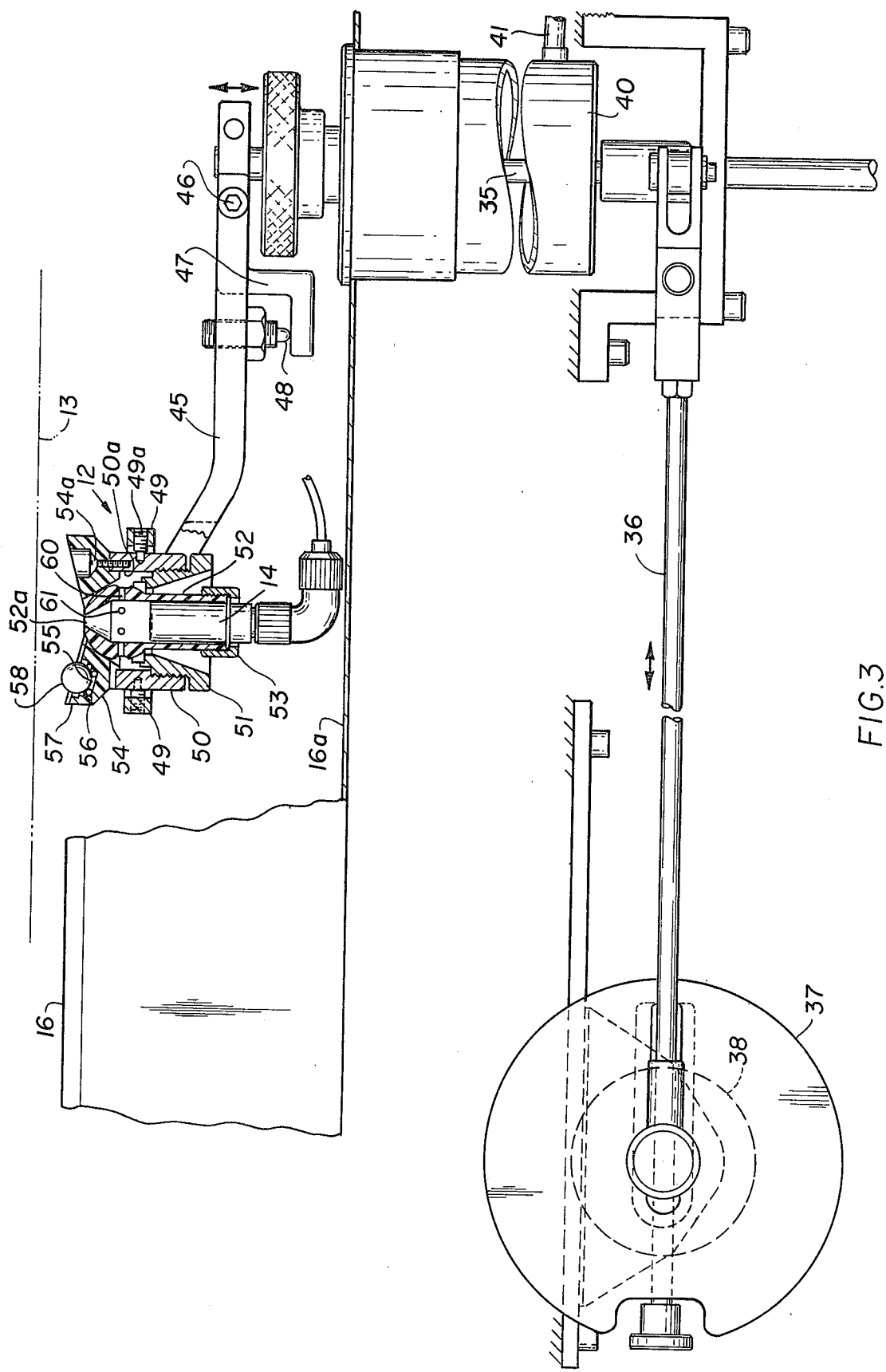
FIG. 3 is a cross-sectional view through the line 3—3 of FIG. 2.

Turning now to FIG. 3 in detail, the ultrasonic head assembly 12 comprises an annular body 50 having a central bore 50A, counterbored and tapped to receive a threaded retaining ring 51 which serves to clamp in place mount 52 for receiving and adjustably supporting and locating the ultrasonic transducer 14. The body is pivotally supported on gimbal ring 49 by means of two opposed pins 49a, and the gimbal ring is, in turn, pivotally supported by two opposed pins 45A from the opposed arms of yoke assembly 45. Pins 49A extend in one plane which is normal to the plane in which the pins 45A extend thereby leaving the body 50 free to tilt omnidirectionally relative to the yoke assembly 45.

The end of mount 52 presented toward the part 13 is generally spherical in outline to facilitate orienting the mount 52 for focusing the transducer 14 relative to the surface of the part 13. The mount 52 has a central longitudinal bore 52A which communicates with the space directly above a receiver member 54 connected to the upwardly presented end (as viewed) of body 50 by means of screws 54A. The receiver member 54 is recessed as shown at 55 in FIG. 3 to receive a plurality of relatively large balls 58, four in the present embodiment with a recess 55 being provided for each, preferably made of a resilient material characterized by a relatively high coefficient of friction such as polyurethane. Each of the balls 58 is held in place by a retainer 57 and is backed by a plurality of relatively small balls 56, preferably formed of polytetrafluoroethylene, in an annular array in the bottom of each of the recesses 55. Each of the retainers 57 is connected to the receiver member 54 by screws 57A. In the embodiment shown, balls 58, about ½ inch in diameter, and balls 56, about ⅛ inch in diameter, have provided the desired contact between the head assembly 12 and the surface of the part 13, with about nine of the smaller balls 56 for each of the larger balls 58.

With transducer mount 52 locked in place in the body 50 against the receiver 54 by retaining ring 51, the bore 50A is sealed except that it is in communication with the space above the receiver 54 through bores 60 which open at holes 61 into the bore 52A. The bore 50A is also in communication with a connector 59 which is also connected through an electrically controlled valve with a source of water under suitable pressure. The lower portion of the bore 52A is closed by the body of transducer 14 and retaining nut 53.

It should be noted that any suitable material can be used in fabricating the parts of the ultrasonic head assembly 12. As shown, the body 50 and retaining ring 51 are made of metal such as stainless steel while mount 52 and receiver 54 are preferably made of a plastic.

In operation, the transducer 14 is connected in the usual way to a suitable ultrasonic pulse generator and receiver, the output from the latter of which is converted to a D.C. voltage representative of the time lapse corresponding to the thickness of the part, and that D.C. voltage is converted to a thickness measurement in the units desired, e.g. mils. Such arrangements are well known and will not be described in detail here. However, it may be well to note that one ultrasonic micrometer which has provided good results is Model 722 manufactured by Erdman Instruments Inc., Pasadena, California.

To put the system into operation, the tail carriage assembly 20 is positioned along tie bar 19 at the proper distance to accommodate the length of part 13 between its idler spindle 26 and the drive spindle 25 on the drive carriage assembly 17, the latter being positioned at one end, say the right, of its travel along rail 15. With the various motors de-energized, the water supply to the ultrasonic head assembly 12 through connector 59 is turned on, and the air cylinder 40 is actuated to raise the yoke assembly 45 to bring the freely rotatable balls 58 into engagement with the surface of the part 13. The transducer 14 is energized by the ultrasonic micrometer (not shown), and the shape of the reflected pulses received by the micrometer is examined on an oscilloscope. If necessary, the position of the transducer 14 relative to the surface of part 13 is adjusted by loosening retaining nut 53 to shift it axially and/or by loosening the retaining ring 51 to shift the angle of the axis of the transducer 14 relative to the plane of the surface of the part 13. When the ultrasonic waves are properly focused, the ring 51 and nut 53 are tightened and the equipment is put into operation. When the part 13 has a non-circular cross section, then instead of energizing both cable drive motor 21 and spindle drive motor 27, the latter is left de-energized, and instead, the crank motor 38 is energized to oscillate the yoke assembly 45 and the ultrasonic head assembly 12 carried thereby. In the case of non-circular parts, each side thereof is scanned by utilizing the manual clutch 29 to rotate the part the desired amount and the operation is repeated as many times for each such part as it has sides to be scanned.

An important advantage of the apparatus of the present invention resides in the manner the ultrasonic head assembly 12, once positioned with its balls 58 engaging the surface of the part 13, freely follows such contours and irregularities as may be present in the surface or the shape of the part. This freedom is ensured by the full gimbal mounting of the head assembly 12 in its yoke 45. This unique degree of mobility is provided while maintaining a continuous column of water between the transducer 14 and the surface of the part 13 to minimize the possibility of spurious signals, and, at the same time, eliminate the need for fully immersing the part 13 in water. Because the balls 58 provide a free rolling contact with the surface of the part 13, marring of the part's surface is substantially completely eliminated.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

What we claim is:

1. An apparatus for ultrasonically inspecting a part, comprising an ultrasonic head assembly including a transducer, a plurality of relatively large bearing bodies rotatably mounted in and projecting from the surface of said head assembly, a plurality of arrays of relatively small bearing bodies one for each of said large bearing bodies and rotatably supporting the same, means for selectively adjusting the distance and inclination between said transducer and said large bearing bodies to a predetermined relationship, means for supporting and resiliently biasing said ultrasonic head assembly for placing said large bearing bodies into engagement with the surface of said part, means for maintaining a substantially continuous column of water between said transducer and the surface of said part, and means for displacing said part and said ultrasonic head assembly relative to each other.

2. An ultrasonic apparatus as set forth in claim 1 in which said surface of said ultrasonic head assembly has a plurality of recesses formed therein one for each of said large bearing bodies, each of said large bearing bodies being a relatively large ball positioned in and projecting from one of said recesses, each of said small bearing bodies being a relatively small ball with one array thereof for each of said recesses and rotatably supporting the large ball located therein.

3. An ultrasonic apparatus as set forth in claim 2 in which means are provided for oscillating said ultrasonic head assembly when a non-circular part is being inspected, and which comprises part supporting means including means for rotating said part about its longitudinal axis.

4. An ultrasonic apparatus as set forth in claim 3 in which said means for supporting said ultrasonic head assembly includes gimbal support means, a gimbal ring pivotally connected to opposed sides of said gimbal support means so as to be free to swing about a first axis extending in one direction, means pivotally connecting said ultrasonic head assembly to said gimbal ring so as to be free to swing about an axis perpendicular to said first axis.

5. An ultrasonic apparatus as set forth in claim 4 in which said gimbal support means has a bifurcated portion forming a yoke having opposed arms, and said gimbal ring is pivotally connected to said arms.

6. An ultrasonic apparatus as set forth in claim 4 in which said ultrasonic head assembly comprises a body having a bore formed therein, a mount having a central bore for receiving said transducer and releasably clamped in said body with one end thereof presented toward said large bearing bodies, said one end of said mount being spherically shaped to facilitate adjustment of the inclination of the mount and the transducer carried thereby.

7. An ultrasonic apparatus as set forth in claim 6 in which said part supporting means further includes an elongated rail, a drive carriage assembly including a drive spindle movably supported on said rail, a tie bar carriage assembly movably supported on said rail, an elongated tie bar extending between and connected to said drive and said tie bar carriage assemblies, a tail carriage assembly including an idler spindle movably supported on said rail and along said tie bar, said tail carriage assembly including means for releasably fixing the same in any desired position along said tie bar so that the opposite ends of a part to be measured can be engaged by said spindles.

* * * * *